(12) United States Patent
Alkon

(10) Patent No.: US 9,833,435 B2
(45) Date of Patent: Dec. 5, 2017

(54) COMPOSITIONS AND METHODS TO TREAT NIEMANN-PICK DISEASE

(71) Applicant: Daniel L. Alkon, Chevy Chase, MD (US)

(72) Inventor: Daniel L. Alkon, Chevy Chase, MD (US)

(73) Assignee: Blanchette Rockefeller Neurosciences Institute, Morgantown, WV (US)

( * ) Notice: Subject to any disclaimer, the term of this patent is extended or adjusted under 35 U.S.C. 154(b) by 0 days.

(21) Appl. No.: 15/126,339

(22) PCT Filed: Mar. 27, 2015

(86) PCT No.: PCT/US2015/023090
§ 371 (c)(1),
(2) Date: Sep. 15, 2016

(87) PCT Pub. No.: WO2015/148975
PCT Pub. Date: Oct. 1, 2015

(65) Prior Publication Data
US 2017/0079948 A1    Mar. 23, 2017

Related U.S. Application Data

(60) Provisional application No. 61/971,480, filed on Mar. 27, 2014.

(51) Int. Cl.
*A61K 31/335* (2006.01)
*A61K 31/365* (2006.01)

(52) U.S. Cl.
CPC .................. *A61K 31/365* (2013.01)

(58) Field of Classification Search
CPC .................................................. A61K 31/365

USPC ......................................................... 514/450
See application file for complete search history.

(56) References Cited

U.S. PATENT DOCUMENTS

2015/0094363 A1* 4/2015 Alexander ........... A61K 31/365
514/450

FOREIGN PATENT DOCUMENTS

WO    WO 2004/004641 A2    1/2004

OTHER PUBLICATIONS

Farshad et al., "PKC Activation in Niemann Pick C1 Cells Restores Subcellular Cholesterol Transport," Plos One, vol. 8, No. 8 Aug. 15, 2013.
Anonymous, "Neurotrope Enters Collaborative Agreement with Icahn School of Medicine at Mount Sinai for use of Bryostatin-1 in the Treatment of Niemann-Pick Disease Type C," Retrieved from the Internet: URL:http://www.finanznachrichten.de/nachrichten-2014-07/30907504-neurotrope-enters-collaborative-agreement-wth-icahn-school-of-medicien-at-mount-sinai-for-use-of-bryostain-1-in-the-treatment-of-niemann-pick-diseas-08 htm, p. 1, paragraph 4, May 11, 2015, page.
International Search Report & Written Opinion, PCT/US2015/023090, dated May 21, 2015.

* cited by examiner

*Primary Examiner* — Raymond Henley, III
(74) *Attorney, Agent, or Firm* — Finnegan, Henderson, Farabow, Garrett & Dunner LLP

(57) ABSTRACT

The present disclosure is directed to compositions comprising bryostatin-1, and methods comprising administering a composition comprising bryostatin-1, to treat Niemann-Pick Type C in a subject in need thereof.

4 Claims, 8 Drawing Sheets

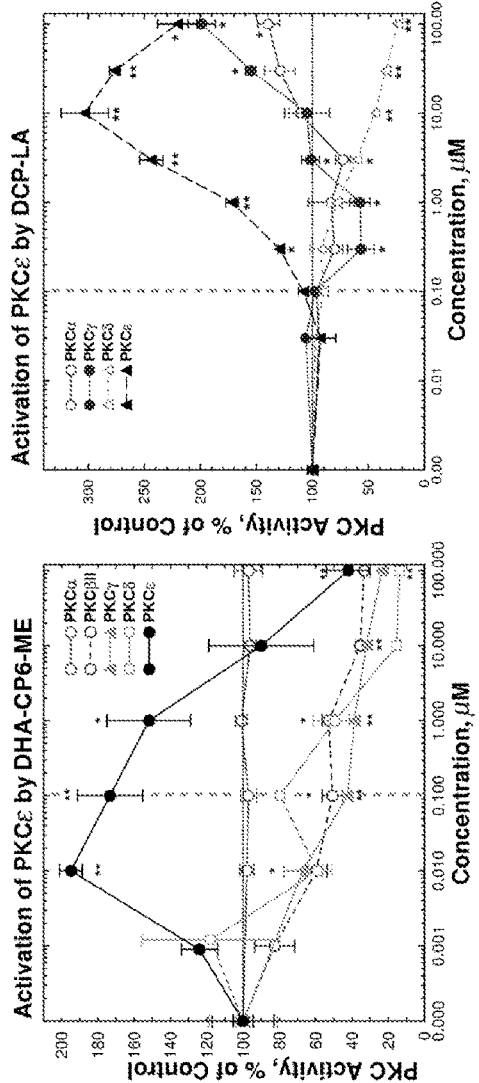
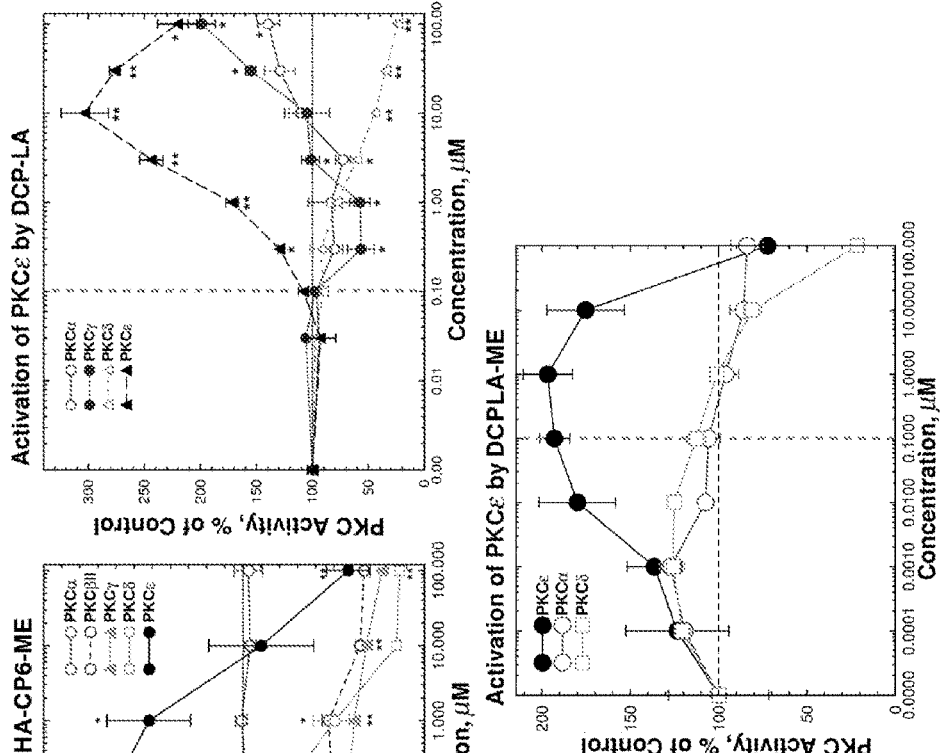
FIG. 4A
FIG. 4B
FIG. 4C

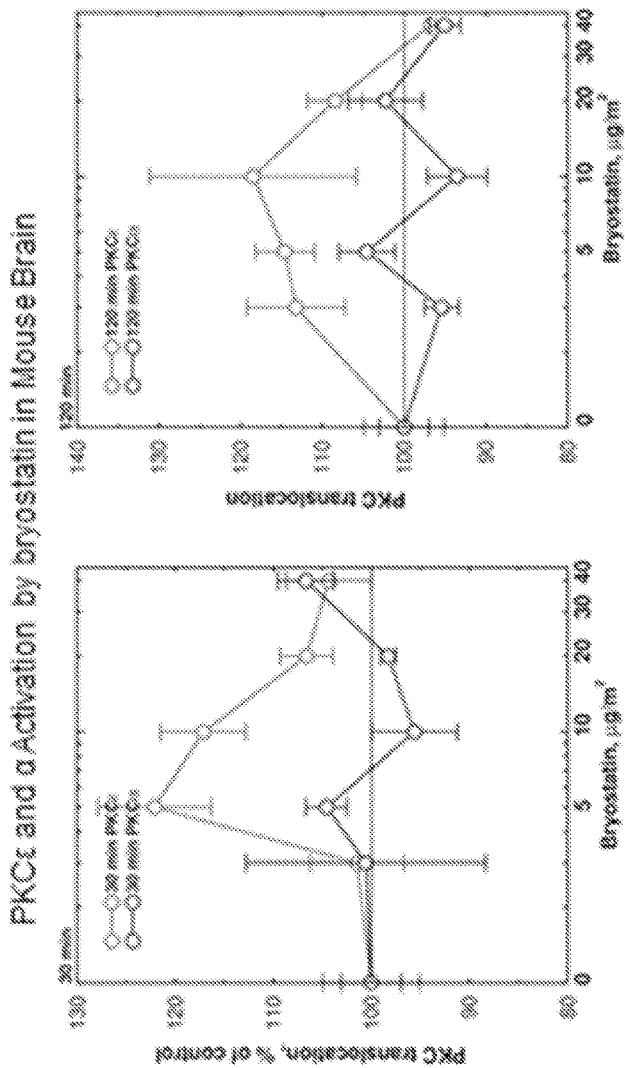

Table II. Relative Band Density of PKC Isoenzymes in Various Tissues of the Rat as Detected by Western Blot Analysis

| Isoenzymes | Relative density in organs* arbitrary units | | | | | | | |
|---|---|---|---|---|---|---|---|---|
| | Brain | Lung | Heart | Spleen | Liver | Testes | Ovary | Kidney |
| α | 3 | 4 | 1 | 5 | 1 | 2 | 2 | 2 |
| β1 | 5 | 1 | 1 | 3 | ND | 1† | 1 | ND |
| β2 | 5 | 1 | 1 | 4 | ND | 1 | 1 | 1 |
| γ | 5 | ND | ND | ND | ND | ND | ND | ND |
| δ | 5 | 4 | 3 | 5 | 2 | 1 | 3 | 1 |
| ε | 5 | ND | ND | ND | ND | ND | ND | 3 |
| ζ | 3 | 5 | 1 | 2 | 4 | 2 | 2 | 3 |

* Equal amounts of protein were loaded from each organ as described in Materials and Methods. The numbers indicate the relative density of immunostaining with 5 being highest and 1 the least detectable staining.
† Strong specific staining of a 39-kD band was detected in testes.
ND, no staining detected.

The Journal of Cell Biology, Volume 117, 1992

FIG. 8

COMPOSITIONS AND METHODS TO TREAT NIEMANN-PICK DISEASE

This application claims priority to U.S. Provisional Patent Application No. 61/971,480, filed Mar. 27, 2014, the contents of which are incorporated herein by reference.

Niemann-Pick Type C (NPC) is an inherited metabolic disorder known as a lipid storage disease. It is caused by mutations in the NPC1 or NPC2 gene. The proteins produced from these genes are involved in the movement of lipids, such as cholesterol, between cells. The gene mutations disrupt the transport of cholesterol and other lipids between cells resulting in excessive accumulation of lipids within tissues and organs, eventually leading to cell death and the malfunction of major organ systems, including the brain. The progressive deterioration of the nervous system is ultimately fatal. NPC may appear early in life or develop in the teen or adult years. Affected individuals have moderate enlargement of the spleen and liver, and brain damage may be extensive and cause an inability to look up and down, difficulty in walking and swallowing, and progressive loss of vision and hearing. NINDS Niemann-Pick Disease Information Page, available at http://www.ninds.nih.gov/disorders/niemann/niemann.htm; Niemann-Pick disease, available at http://ghr.nlm.nih.gov/condition/niemann-pick-disease.

There is currently no cure for NPC. Thus, there is a need to develop therapeutic agents to treat and/or minimize its associated symptoms. Further, it has been reported that the intermediate filament vimentin is hypophosphorylated in NPC-diseased cells compared to Wt cells and that this hypophosphorylation results from reduced protein kinase C (PKC) activity, in particular the $\alpha$, $\epsilon$, and $\beta$II isoforms. Tamari et al., PKC Activation in Niemann Pick C1 Cells Restores Subcellular Cholesterol Transport, PLOS ONE, Vol. 8, Iss. 8 (2013). As Tamari et al. explain, cells lacking vimentin are unable to transport LDL-derived cholesterol from their lysosomes to the endoplasmic reticulum for esterification, and decreased vimentin phosphorylation reduces the pool of soluble vimentin. Id. Increased PKC expression, in particular, the $\alpha$, $\epsilon$, and/or $\beta$II isozymes, phosphorylates vimentin and increases levels of soluble vimentin in NPC-diseased cells, ameliorating the cholesterol transport block. Id. As shown in FIGS. 7 and 8, PKC $\epsilon$ and $\alpha$ have been substantially detected in the brain (Wetsel et al., Journal of Cell Biology, Vol. 117, 1992), which suffers progressively significant degeneration in NPC. Thus, there is a further need to discover and develop agents that act as potent activators of particular PKC isoforms, such as PKC $\epsilon$ and/or $\alpha$, to treat Niemann-Pick disease.

Accordingly, the present disclosure is directed to a composition comprising bryostatin-1 in an effective amount to treat NPC, wherein the effective amount results in a concentration of bryostatin-1 in the brain of a subject in need of treatment ranging from about 0.1 nM to about 1.5 nM.

The present disclosure is also directed to a method for treating NPC in a subject in need of treatment, comprising administering to the subject a composition comprising bryostatin-1 in an amount effective to treat NPC, wherein the effective amount results in a concentration of bryostatin-1 in the brain ranging from about 0.1 nM to about 1.5 nM.

Additional advantages of the disclosure will be set forth in part in the description which follows, and in part will be obvious from the description, or may be learned by practice of the invention. The advantages of the disclosure will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the disclosure and together with the description, serve to explain the principles of the disclosure.

BRIEF DESCRIPTION OF THE DRAWINGS

FIGS. 4A-4C show PKC isozyme activation by other PKC activators (DHA-CP6-ME (4A), DCP-LA (4B) and DCPLA-ME (4C)) at various concentrations.

FIGS. 5A and 5B show PKC-$\epsilon$ and PKC-$\alpha$ activation by bryostatin-1 in mouse brain at various doses after 30 minutes or 120 minutes.

FIG. 8 shows the relative abundance of PKC isozymes in rat tissue, as provided in Wetsel et al., Journal of Cell Biology, Vol. 117 (1992).

DESCRIPTION

Figure 1:
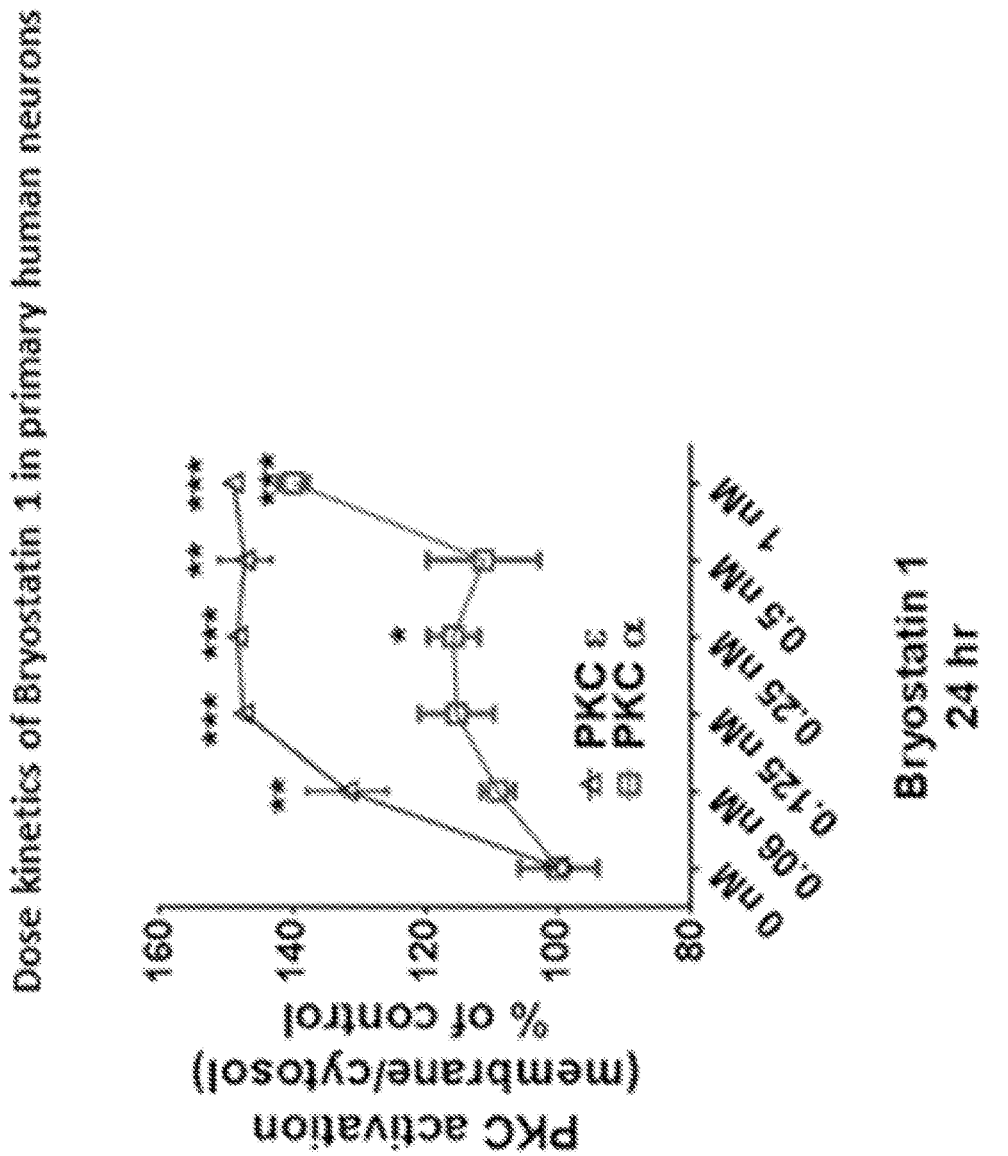
FIG. 1 shows dose kinetics and PKC isozyme specificity of bryostatin-1 in primary human neurons.

Particular aspects of the disclosure are described in greater detail below. The terms and definitions as used in the present application and as clarified herein are intended to represent the meaning within the present disclosure. The patent and scientific literature referred to herein is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value including an acceptable degree of error for the quantity measured given the nature or precision of the measurements. As used herein, the terms "approximately" and "about" should be generally understood to encompass ±20% of a specified amount, frequency or value. Numerical quantities given herein are approximate unless stated otherwise, meaning that term "about" or "approximately" can be inferred when not expressly stated.

The terms "administer," "administration," or "administering" as used herein refer to (1) providing, giving, dosing and/or prescribing by either a health practitioner or his authorized agent or under his direction a composition according to the disclosure, and/or (2) putting into, taking or consuming by the patient or person himself or herself, a composition according to the disclosure. As used herein, "administration" of a composition includes any route of administration, including oral, intravenous, subcutaneous, intraperitoneal, and intramuscular.

As used herein, the term "subject" means a mammal, i.e., a human or a non-human mammal.

As used herein, "protein kinase C activator" or "PKC activator" means a substance that increases the rate of the reaction catalyzed by protein kinase C by binding to the protein kinase C.

The term "pharmaceutically acceptable" refers to molecular entities and compositions that are physiologically tolerable and do not typically produce untoward reactions when administered to a subject.

Protein kinase C (PKC) is one of the largest gene families of non-receptor serine-threonine protein kinases. Since the discovery of PKC in the early eighties and its identification as a major receptor for phorbol esters, a multitude of physiological signaling mechanisms have been ascribed to this enzyme. Kikkawa et al., *J. Biol. Chem.* (1982), vol. 257, pp. 13341-13348; Ashendel et al., *Cancer Res.* (1983), vol. 43: 4333-4337. The interest in PKC stems from its unique ability to be activated in vitro by calcium and diacylglycerol (and phorbol ester mimetics), an effector whose formation is coupled to phospholipid turnover by the action of growth and differentiation factors. Activation of PKC involves binding of 1,2-diacylglycerol (DAG) and/or 1,2-diacyl-sn-glycero-3-phospho-L-serine (phosphatidyl-L-serine, PS) at different binding sites. An alternative approach to activating PKC directly is through indirect PKC activation, e.g., by activating phospholipases such as phospholipase C$\gamma$, by stimulating the Ser/Thr kinase Akt by way of phosphatidylinositol 3-kinase (PI3K), or by increasing the levels of DAG, the endogenous activator. Nelson et al., *Trends in Biochem. Sci.* (2009) vol. 34, pp. 136-145. Diacylglycerol kinase inhibitors, for example, may enhance the levels of the endogenous ligand diacylglycerol, thereby producing activation of PKC. Meinhardt et al., *Anti-Cancer Drugs* (2002), vol. 13, pp. 725-733. Phorbol esters, however, are not suitable compounds for eventual drug development because of their tumor promotion activity. Ibarreta et al. *Neuroreport* (1999), vol. 10, pp. 1035-1040).

The PKC gene family consists of 11 genes, which are divided into four subgroups: (1) classical PKC $\alpha$, $\beta$1, $\beta$2 ($\beta$1 and $\beta$2 are alternatively spliced forms of the same gene) and $\gamma$; (2) novel PKC $\delta$, $\epsilon$, $\eta$, and $\theta$; (3) atypical PKC $\zeta$ and $\iota/\lambda$; and (4) PKC$_\mu$. PKC$_\mu$ resembles the novel PKC isoforms but differs by having a putative transmembrane domain. Blobe et al. *Cancer Metastasis Rev.* (1994), vol. 13, pp. 411-431; Hug et al. *Biochem. J.* (1993) vol. 291, pp. 329-343; Kikkawa et al. *Ann. Rev. Biochem.* (1989), vol. 58, pp. 31-44. The classical PKC isoforms $\alpha$, $\beta$1, $\beta$2, and $\gamma$ are Ca$^{2+}$, phospholipid, and diacylglycerol-dependent, whereas the other isoforms are activated by phospholipid, diacylglycerol but are not dependent on Ca$^{2+}$ and no activator may be necessary. All isoforms encompass 5 variable (VI-V5) regions, and the $\alpha$, $\beta$, and $\gamma$ isoforms contain four (C1-C4) structural domains which are highly conserved. All isoforms except PKC $\alpha$, $\beta$, and $\gamma$ lack the C2 domain, the $\iota/\lambda$ and $\eta$ isoforms also lack nine of two cysteine-rich zinc finger domains in C1 to which diacylglycerol binds. The C1 domain also contains the pseudosubstrate sequence which is highly conserved among all isoforms, and which serves an autoregulatory function by blocking the substrate-binding site to produce an inactive conformation of the enzyme. House et al., *Science* (1987), vol. 238, pp. 1726-1728.

Because of these structural features, diverse PKC isoforms are thought to have highly specialized roles in signal transduction in response to physiological stimuli as well as in neoplastic transformation and differentiation. Nishizuka, *Cancer* (1989), vol. 10, pp. 1892-1903; Glazer, pp. 171-198 in *Protein Kinase C*, I. F. Kuo, ed., Oxford U. Press, 1994. For a discussion of PKC modulators see, for example, International Application No. PCT/US97/08141 (WO 97/43268) and U.S. Pat. Nos. 5,652,232; 6,080,784; 5,891,906; 5,962,498; 5,955,501; 5,891,870 and 5,962,504, each incorporated by reference herein in its entirety.

PKC activators can be broad-spectrum activators, acting on multiple isoforms of PKC, or can be selective for certain isoforms. Selective PKC activators may offer unique advantages because different isoforms can perform different functions. It has been shown that increased PKC expression of the $\alpha$, $\epsilon$, and/or $\beta$II isoforms phosphorylates vimentin and increases levels of soluble vimentin in Niemann-Pick diseased cells, ameliorating the cholesterol transport block associated with the disease. Tamari et al., PKC Activation in Niemann Pick C1 Cells Restores Subcellular Cholesterol Transport, PLOS ONE, Vol. 8, Iss. 8 (2013). The present inventor has discovered that a concentration of bryostatin-1 in the brain within the range of 0.1 nM to 1.5 nM results in a PKC isozyme activation signature (i.e., the activation of specific PKC isozymes, including PKC $\epsilon$ and/or $\alpha$) that is particularly advantageous for treating NPC.

Thus, in one aspect of the present disclosure, a composition comprises bryostatin-1 in an effective amount to treat NPC, wherein the effective amount results in a concentration of bryostatin-1 in the brain of a subject in need of treatment ranging from about 0.1 nM to about 1.5 nM. For example, in some embodiments, the effective amount results in a concentration of bryostatin-1 in the brain of about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.1 nM, about 1.2 nM, about 1.3 nM, about 1.4 nM, about 1.5 nM, or any value in between.

The blood plasma concentration of bryostatin-1 corresponds to about five times the concentration of bryostatin-1 in the brain. Thus, in some embodiments, an effective amount of bryostatin-1 to treat NPC results in a blood plasma concentration of about 0.5 nM to about 7.5 nM. For example, in some embodiments, the effective amount of bryostatin-1 results in a blood plasma concentration of bryostatin-1 of about 0.5 nM, about 1 nM, about 1.5 nM, about 2 nM, about 2.5 nM, about 3 nM, about 3.5 nM, about 4 nM, about 4.5 nM, about 5 nM, about 5.5 nM, about 6 nM, about 6.5 nM, about 7 nM, about 7.5 nM, or any value in between.

In some embodiments, the effective amount of bryostatin-1 to treat NPC ranges from about 5 $\mu$g/m$^2$ to about 120 $\mu$g/m$^2$. For example, in some embodiments, the effective amount of bryostatin-1 to treat NPC is about 5 $\mu$g/m$^2$, about 10 $\mu$g/m$^2$, about 15 $\mu$g/m$^2$, about 20 $\mu$g/m$^2$, about 25 $\mu$g/m$^2$, about 30 $\mu$g/m$^2$, about 35 $\mu$g/m$^2$, about 40 $\mu$g/m$^2$, about 45 $\mu$g/m$^2$, about 50 $\mu$g/m$^2$, about 55 $\mu$g/m$^2$, about 60 $\mu$g/m$^2$, about 65 $\mu$g/m$^2$, about 70 $\mu$g/m$^2$, about 75 $\mu$g/m$^2$, about 80 $\mu$g/m$^2$, about 85 $\mu$g/m$^2$, about 90 $\mu$g/m$^2$, about 95 $\mu$g/m$^2$, about 100 $\mu$g/m$^2$, about 105 $\mu$g/m$^2$, about 110 $\mu$g/m$^2$, about 115 $\mu$g/m$^2$, about 120 $\mu$g/m$^2$, or any value in between.

In some embodiments, the concentrations of bryostatin-1 disclosed herein are peak concentrations of bryostatin-1.

Formulations of the pharmaceutical compositions described herein may be prepared by any suitable method known in the art of pharmacology. In general, such preparatory methods include bringing the active ingredient, i.e., bryostatin-1, into association with a carrier or one or more other accessory ingredients, then, if necessary or desirable, shaping or packaging the product into a desired single- or multi-dose unit.

Although the descriptions of pharmaceutical compositions provided herein are principally directed to pharmaceutical compositions suitable for ethical administration to humans, it will be understood by skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

In one embodiment, the compositions disclosed herein may be formulated with a pharmaceutically acceptable carrier for administration. Pharmaceutically acceptable carriers include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other additional ingredients that may be included in the pharmaceutical compositions of the disclosure are generally known in the art and may be described, for example, in *Remington's Pharmaceutical Sciences*, Genaro, ed., Mack Publishing Co., Easton, Pa., 1985, and *Remington's Pharmaceutical Sciences*, 20$^{th}$ Ed., Mack Publishing Co. 2000, both incorporated by reference herein.

In one embodiment, the carrier is an aqueous or hydrophilic carrier. In a further embodiment, the carrier can be water, saline, or dimethylsulfoxide. In another embodiment, the carrier is a hydrophobic carrier. Hydrophobic carriers include inclusion complexes, dispersions (such as micelles, microemulsions, and emulsions), and liposomes. Exemplary hydrophobic carriers include inclusion complexes, micelles, and liposomes. See, e.g., Remington's: The Science and Practice of Pharmacy 20th ed., ed. Gennaro, Lippincott: Philadelphia, Pa. 2003, incorporated by reference herein. In addition, other compounds may be included either in the hydrophobic carrier or the solution, e.g., to stabilize the formulation.

The composition disclosed herein may be administered by any suitable route including oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration. A suitable route of administration may be chosen to permit crossing the blood-brain barrier. Rapoport et al., *J. Lipid Res.* (2001) vol. 42, pp. 678-685.

The composition may be formulated according to conventional methods, and may include any pharmaceutically acceptable additives, such as excipients, lubricants, diluents, flavorants, colorants, buffers, and disintegrants. See e.g., Remington's Pharmaceutical Sciences, 20$^{th}$ Ed., Mack Publishing Co. 2000.

In some embodiments, the composition disclosed herein is formulated in a solid oral dosage form. For oral administration, the composition may take the form of a tablet or capsule prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods generally known in the art.

In some embodiments, the composition is formulated into a liquid preparation. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-phydroxybenzoates or sorbic acid). The preparations may also comprise buffer salts, flavoring, coloring and sweetening agents as appropriate.

In other embodiments of the present disclosure, the composition may be formulated for parenteral administration such as bolus injection or continuous infusion. Formulations for injection may be presented in unit dosage form, e.g., in ampoules or in multi-dose containers, with an added preservative. The composition may take such forms as suspensions, solutions, dispersions, or emulsions in oily or aqueous vehicles, and may contain formulatory agents such as suspending, stabilizing and/or dispersing agents.

In some embodiments, the composition may be formulated as a depot preparation. Such formulations may be administered by implantation (for example subcutaneously or intramuscularly) or by intramuscular injection. For example, the composition may be formulated with suitable polymeric or hydrophobic material (for example as an emulsion in an acceptable oil) or ion exchange resins, or as sparingly soluble derivatives, for example, as a sparingly soluble salt.

In another embodiment, the composition may be delivered in a vesicle, such as a micelle, liposome, or an artificial low-density lipoprotein (LDL) particle. See, e.g., U.S. Pat. No. 7,682,627.

In another aspect, the present disclosure is directed to a method for treating NPC in a subject in need of treatment, comprising administering to the subject a composition comprising bryostatin-1 in an effective amount to treat NPC, wherein the effective amount results in a concentration of bryostatin-1 ranging from about 0.1 nM to about 1.5 nM. For example, in some embodiments, the effective amount results in a concentration of bryostatin-1 in the brain of about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.1 nM, about 1.2 nM, about 1.3 nM, about 1.4 nM, about 1.5 nM, or any value in between.

As described above, the blood plasma concentration of bryostatin-1 corresponds to about five times the concentration of bryostatin-1 in the brain. Thus, in some embodiments, an effective amount of bryostatin-1 to treat NPC results in a blood plasma concentration of about 0.5 nM to about 7.5 nM. For example, in some embodiments, the effective amount of bryostatin-1 results in a blood plasma concentration of bryostatin-1 of about 0.5 nM, about 1 nM, about 1.5 nM, about 2 nM, about 2.5 nM, about 3 nM, about 3.5 nM, about 4 nM, about 4.5 nM, about 5 nM, about 5.5 nM, about 6 nM, about 6.5 nM, about 7 nM, about 7.5 nM, or any value in between.

In some embodiments, the effective amount of bryostatin-1 to treat NPC ranges from about 5 μg/m$^2$ to about 120 μg/m$^2$. For example, in some embodiments, the effective amount of bryostatin-1 to treat NPC is about 5 μg/m$^2$, about 10 μg/m$^2$, about 15 μg/m$^2$, about 20 μg/m$^2$, about 25 μg/m$^2$, about 30 μg/m$^2$, about 35 μg/m$^2$, about 40 μg/m$^2$, about 45 μg/m$^2$, about 50 μg/m$^2$, about 55 μg/m$^2$, about 60 μg/m$^2$, about 65 μg/m$^2$, about 70 μg/m$^2$, about 75 μg/m$^2$, about 80 μg/m$^2$, about 85 μg/m$^2$, about 90 μg/m$^2$, about 95 μg/m$^2$, about 100 μg/m$^2$, about 105 μg/m$^2$, about 110 μg/m$^2$, about 115 μg/m$^2$, about 120 μg/m$^2$, or any value in between.

In some embodiments, the concentrations of bryostatin-1 disclosed herein are peak concentrations of bryostatin-1

The compositions and methods described herein will be further described by the following examples.

EXAMPLES

Example 1

Dose Kinetics and PKC Isozyme Specificity of Bryostatin-1 in Primary Human Neurons PKC isozyme activation by bryostatin-1 at various concentrations in primary human neurons was evaluated. One month old primary human neurons were treated with 0 nM, 0.060 nM, 0.125 nM, 0.25 nM, 0.5 nM and 1.0 nM bryostatin 1 for 24 hr. Neurons were separated into soluble and membrane fractions and immunoblotted against PKC α and PKC ε. PKC activation was measured as the percentage of total protein in the membrane and reported as percentage of control. PKC staining levels were measured densitometrically. Data are represented as mean±SE of three independent experiments (Students t-test, *P<0.05 and **P<0.005).

As shown in the results in FIG. 1, bryostatin-1 activated both PKC ε and PKC α. At low concentrations, bryostatin-1 showed potent PKC ε activation. At about 1 nM, bryostatin-1 exhibited potent activation of both PKC ε and PKC α.

Example 2

Time Kinetics and PKC Isozyme Specificity of 0.25 nM Bryostatin-1 in Primary Human Neurons PKC isozyme activation by bryostatin-1 at 0.25 nM in primary human neurons was evaluated. One month old primary human neurons were treated with ethanol (C), bryostatin 1 (0.25 nM) for 1 hr, 4 hr and 24 hr. Neurons were separated into soluble (S) and membrane (P) fractions and immunoblotted against PKC α, PKC ε and PKC δ. PKC activation was measured as the percentage of total protein in the membrane and reported as percentage of control. PKC staining levels were measured densitometrically.

Figure 2B:
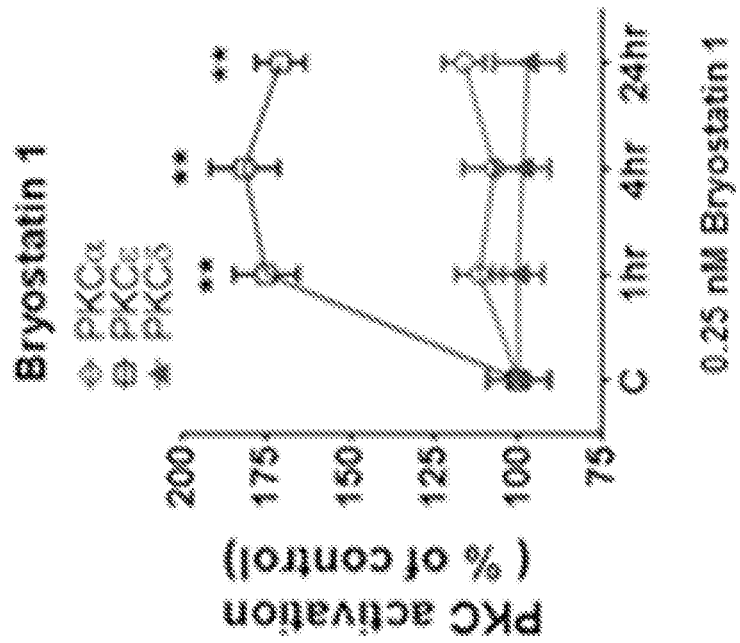
FIGS. 2A and 2B show time kinetics and PKC isozyme specificity of 0.25 nM bryostatin-1 in primary human neurons.
Figure 2A:
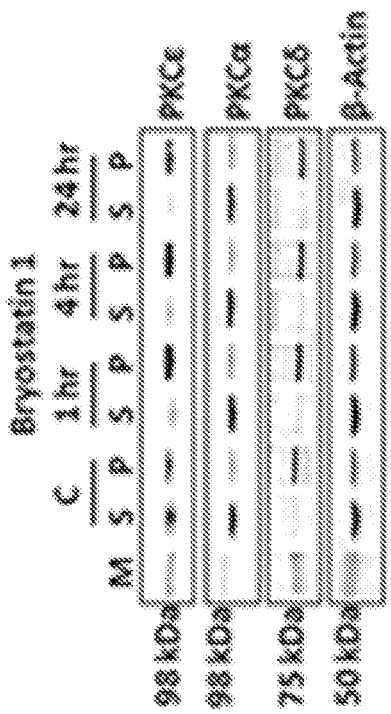

The results are shown in FIG. 2A (Western blot) and FIG. 2B (time course of activation). Bryostatin-1 (F(3,8)=22.5; ANOVA p=0.0003) induced PKC-ε activation at 1 hr, 4 hr and 24 hr. Data are represented as mean±SE of three independent experiments (Students t-test, *P<0.05 and **P<0.005).

Example 3

PKC Isozyme Specificity of 0.27 nM Bryostatin-1 in SH-SY5Y Cells

PKC isozyme activation by bryostatin-1 at 0.27 nM in SH-SY5Y cells was evaluated. SH-SY5Y cells are human-derived cell line and are often used as in vitro models of neuronal function and differentiation. Cells were treated with bryostatin-1 (0.27 nM) for 0, 5, 15, 30 and 60 min. Samples were fractionated into cytosol and membrane fractions and analyzed with PKC isoform-specific antibodies. Three independent experiments were performed for each sample.

Figure 3:
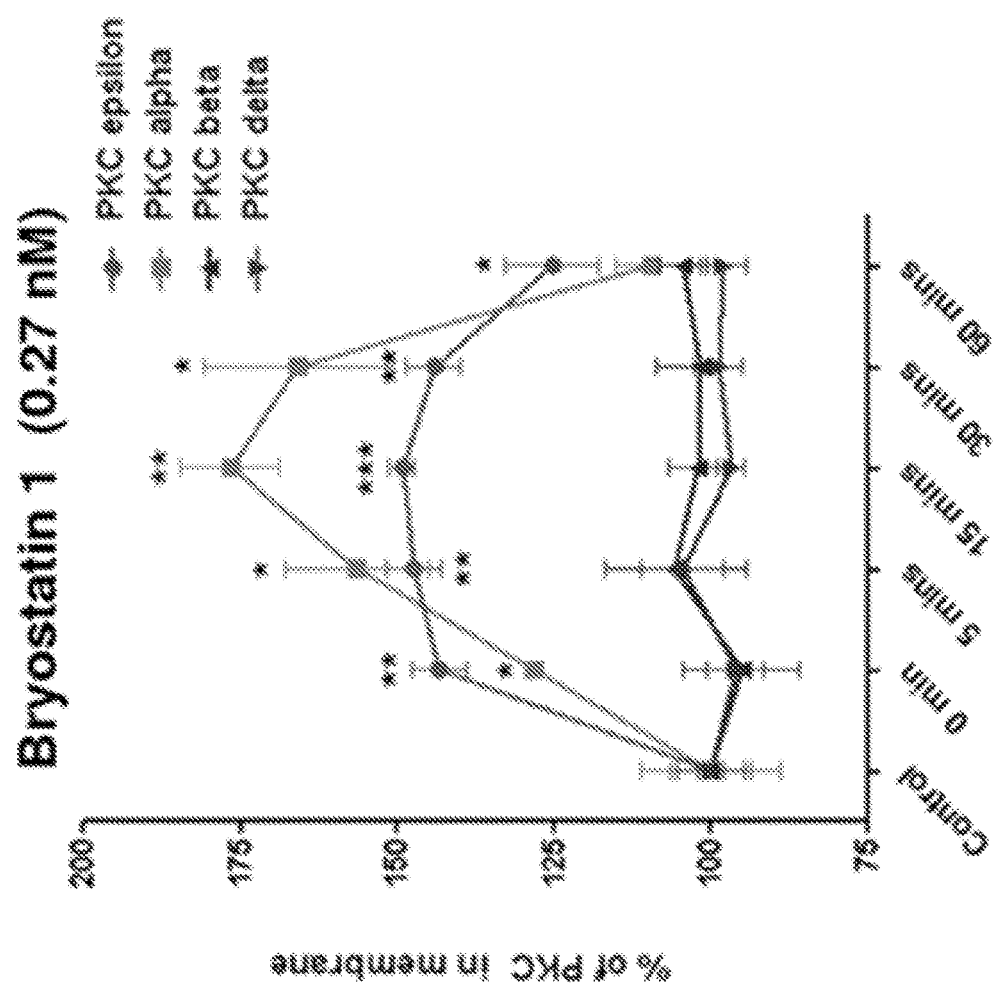
FIG. 3 shows PKC isozyme specificity of 0.27 nM Bryostatin-1 in SH-SY5Y cells.

The results are shown in FIG. 3. Bryostatin-1 activated both PKC ε and PKC α. The data in the graph represent mean±SE. (Students t-test *p<0.05; p<0.005 and *p<0.0005).

Example 4

PKC Isozyme Activation by Other PKC Activators

PKC isozyme activation by other PKC activators was evaluated. FIGS. 4A and 4B show the results for different concentrations of DHA-CP6 methyl ester (a docosahexaenoic acid derivative) and DCPLA (a linoleic acid derivative), respectively:

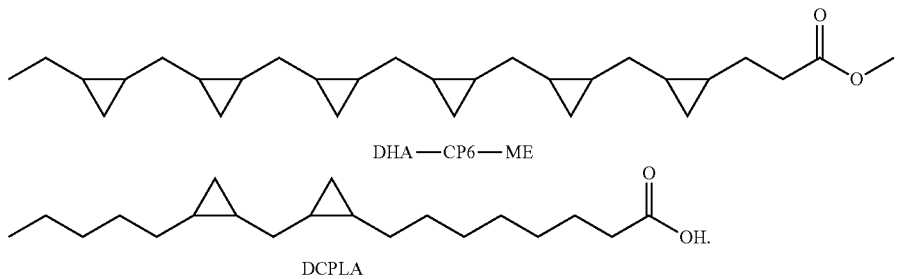

DHA-CP6-ME and DCPLA were incubated with recombinant PKC isozymes (α, βII, γ, δ, and/or ε) for 5 min at 4° C. PKC activity was measured enzymatically by measuring the incorporation of 32P-inorganic phosphate from 32P-ATP into histones.

FIG. 4C shows the results for different concentrations of DCPLA-ME:

For measuring PKC activation, recombinant PKC α, ε, and δ were used. DCPLA-ME induced activation was measured in absence of diacylglycerol (DAG) and phosphatidylserine (PS). Individual enzymes were incubated for 15 min at 37° C. in the presence of 10 uM histones, 4.89 mM CaCl2, 10 mM MgCl2, 20 mM HEPES (pH 7.4), 0.8 mM EDTA, 4 mM EGTA, 4% glycerol, 8 ug/ml aprotinin, 8 ug/ml leupeptin, 2 mM benzamidine and 0.5 uCi of [gamma-32P]ATP. [32P]Phosphoprotein formation was measured by adsorption onto phosphocellulose. Data are represented as mean±SE of three independent experiments (Students t-test, *P<0.05 and **P<0.005).

Example 5

PKC Activation by Bryostatin-1 in Mouse Brain

Mice were injected with bryostatin-1 in DMSO at doses of 3, 5, 10, 20, and 40 μg/m² in the tail vein. After 30 or 120 min, the brains were frozen, then homogenized in 10 mM tris-HCl pH 7.4. The homogenates were fractionated into cytosolic and membrane fractions by ultracentrifugation. Fractions were analyzed by Western blotting using isozyme-specific antibodies. The results are shown in FIG. 5A (30 min) and 5B (120 min).

Example 6

Time Course of PKC Activation by Bryostatin-1 in Mouse Brain

Figure 6B:
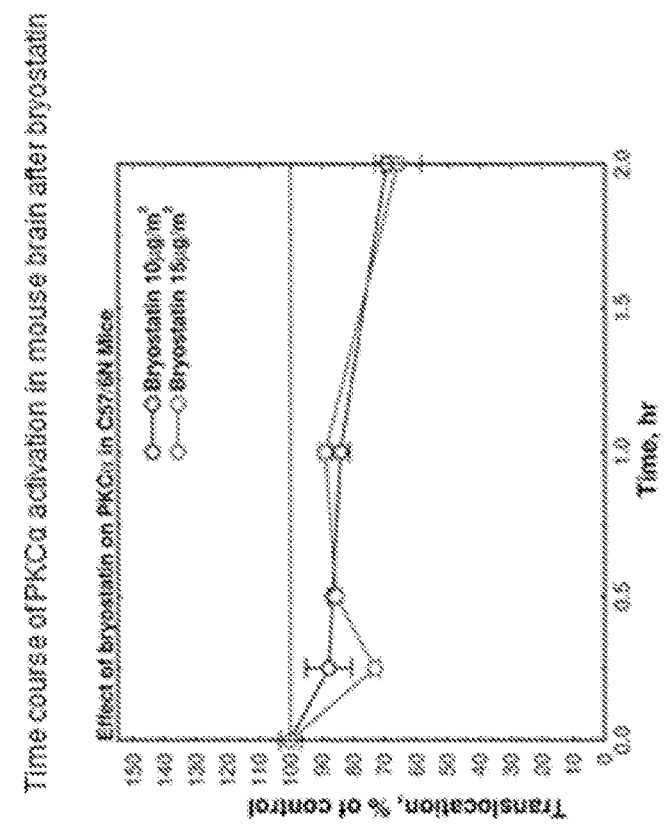
FIG. 6A and 6B show the time course of PKC-$\epsilon$ and PKC-$\alpha$ activation, respectively, by bryostatin-1 in mouse brain at certain doses.
Figure 6A:
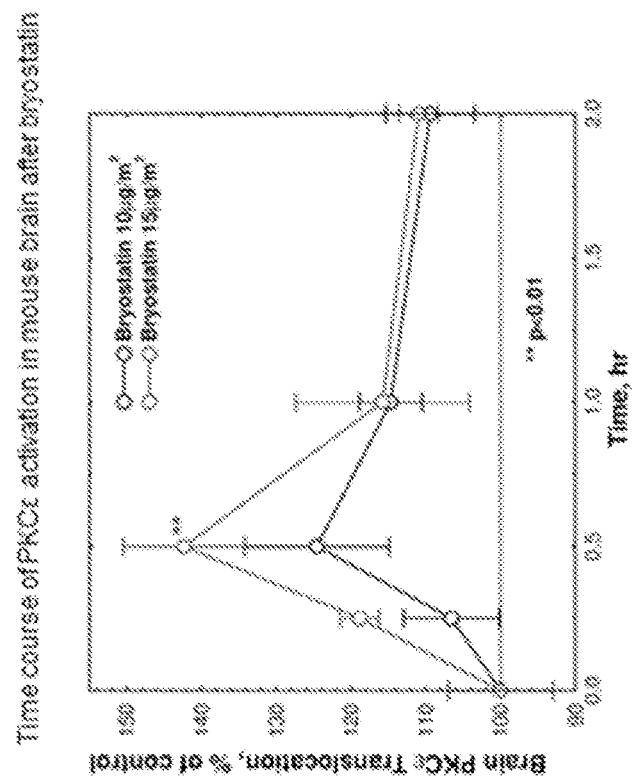
Figure 7:
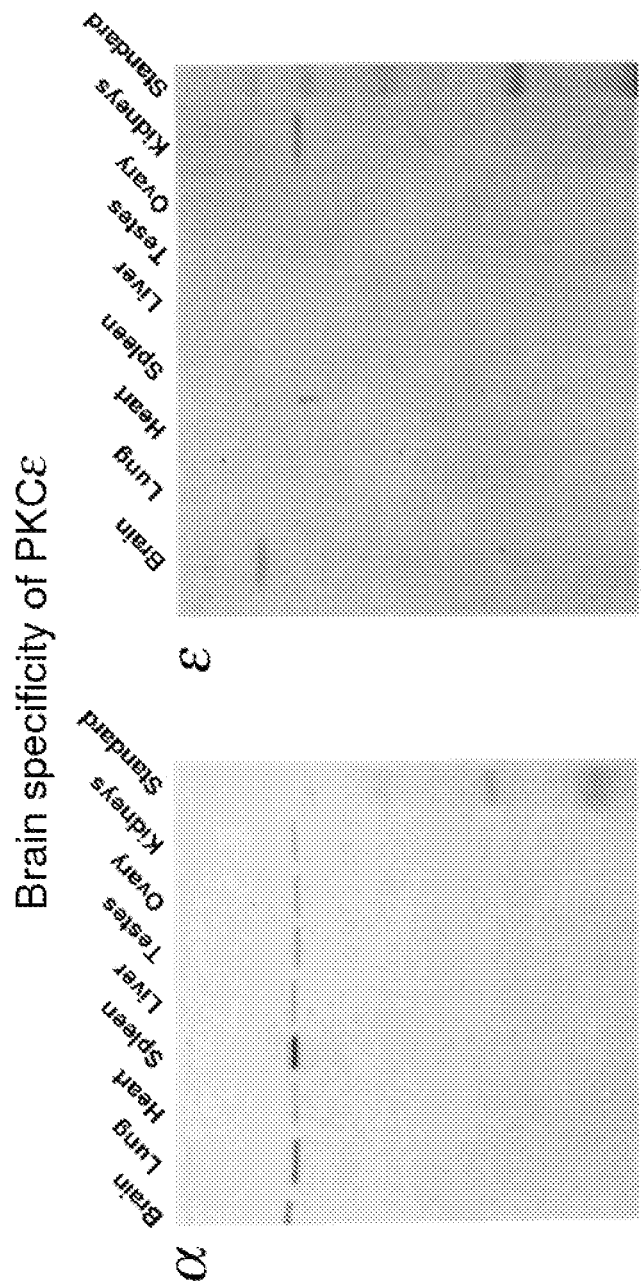
FIG. 7 shows the distribution of PKC $\alpha$ and PKC $\epsilon$ in the body, as provided in Wetsel et al., Journal of Cell Biology, Vol. 117 (1992).

Mice were injected with bryostatin-1 in DMSO at doses of 10 or 15 μg/m² in the tail vein. After 15, 30, 60, or 120 min, the brains were frozen, then homogenized in 10 mM tris-HCl pH 7.4. The homogenates were fractionated into cytosolic and membrane fractions by ultracentrifugation. Fractions were analyzed by Western blotting using PKC epsilon-specific antibodies (FIG. 6A) or PKC alpha-specific antibodies (FIG. 6B). PKC staining levels were measured densitometrically.

Experimental Procedures

Culture of primary human cortical neurons: Human primary neurons (ScienCell Research Laboratories, Carlsbad, Calif., USA) were plated on poly-L-lysine coated plates and were maintained in neuronal medium (ScienCell Research Laboratories, Carlsbad, Calif., USA) supplemented with the neuronal growth supplement (NGS, ScienCell Research Laboratories, Carlsbad, Calif., USA). For maintenance of neurons, half of the media was changed every 3 days. Fresh activators were added with every media change.

Cell culture and treatments: Human SH-SY5Y neuroblastoma cells (ATCC) were cultured in 45% F12K, 45% DMEM and 10% FBS.

Cell lysis and Western blot analysis: Cells were harvested in homogenizing buffer (HB) containing 10 mM Tris-Cl (pH 7.4), 1 mM PMSF (phenylmethylsulfonylfluoride), 1 mM EGTA, 1 mM EDTA, 50 mM NaF and 20 μM leupeptin, and were lysed by sonication. The homogenate was centrifuged at 100,000×g for 15 min at 4° C. to obtain the cytosolic fraction (supernatant) and membrane (pellet). The pellet was resuspended in the HB by sonication. Protein concentration was measured using the Coomassie Plus (Bradford) Protein Assay kit (Pierce, Rockford, Ill., USA). Following quantification, 20 μg of protein from each sample was subjected to SDS-PAGE analysis in a 4-20% gradient Tris-Glycine polyacrylamide gel (Invitrogen, Carlsbad, Calif., USA). The separated protein was then transferred to a nitrocellulose membrane. The membrane was blocked with BSA and incubated with primary antibody overnight at 4° C. After incubation, it was washed 3× with TBS-T (Tris-buffered saline-Tween 20) and further incubated with alkaline phosphatase conjugated secondary antibody at 1:10000 dilution for 45 min. The membrane was finally washed 3× with TBS-T and developed using the 1-step NBT-BCIP substrate (Pierce, Rockford, Ill., USA). The blot was imaged in a ImageQuant RT-ECL (GE Life Sciences, Piscataway, N.J.) and densitometric quantification was performed using IMAL software. For quantifying expression of a protein, the densitometric value for the protein of interest was normalized against beta-actin (loading control).

PKC assay: For measurement of PKC activation by DCPLA-ME, activation of recombinant PKCalpha, PKCepsilon and PKCdelta (Cell Signaling Technology, USA) was used. DCPLA-ME induced activation was measured in absence of diacylglycerol (DAG) and phosphatidylserine (PS). Individual enzymes were incubated for 15 min at 37° C. in the presence of 10 uM histones, 4.89 mM CaCl2, 10 mM MgCl2, 20 mM HEPES (pH 7.4), 0.8 mM EDTA, 4 mM EGTA, 4% glycerol, 8 ug/ml aprotinin, 8 ug/ml leupeptin, 2 mM benzamidine and 0.5 uCi of [gamma-32P]ATP. [32P] Phosphoprotein formation was measured by adsorption onto phosphocellulose.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition comprising bryostatin-1 in an effective amount to treat Niemann-Pick Type C (NPC), wherein the effective amount results in a concentration of bryostatin-1 in the brain of a subject in need of treatment ranging from about 0.1 nM to about 1.5 nM.

2. The composition of claim 1, wherein the effective amount results in a concentration of bryostatin-1 in the brain of about 1 nM.

3. A method for treating Niemann-Pick Type C (NPC) in a subject in need of treatment, comprising administering to the subject a composition comprising bryostatin-1 in an effective amount to treat NPC, wherein the effective amount results in a concentration of bryostatin-1 in the brain ranging from about 0.1 nM to about 1.5 nM.

4. The method of claim 3, wherein the effective amount results in a concentration of bryostatin-1 in the brain of about 1 nM.

* * * * *